US005789202A

United States Patent [19]

Hoskins et al.

[11] Patent Number: 5,789,202

[45] Date of Patent: Aug. 4, 1998

[54] DNA ENCODING A NOVEL PENICILLIN BINDING PROTEIN FROM STREPTOCOCCUS PNEUMONIAE

[75] Inventors: Jo Ann Hoskins; S. Richard Jaskunas, Jr.; Pamela K. Rockey; Paul R. Rosteck, Jr.; Franklin H. Norris, all of Indianapolis, Ind.

[73] Assignee: Eli Lilly and Company, Indianapolis, Ind.

[21] Appl. No.: 731,716

[22] Filed: Oct. 17, 1996

[51] Int. Cl.[6] .......................... C07H 21/04; C12N 15/00; C12N 15/09

[52] U.S. Cl. ..................... 435/69.3; 435/320.1; 435/325; 536/23.7

[58] Field of Search .................................. 536/23.7, 23.5; 435/320.1, 325, 69.3

[56] References Cited

PUBLICATIONS

Dowson, et al., *Molecular Microbiology*, (1989) 3(1), 95–102.

Laible, et al., *Molecular Microbiology*, (1989) 3(10), 1337–1348.

Liable, et al., *Molecular Microbiology*, (1991) 5(8), 1993–2002.

Martin, et al. *Journal of Bacteriology*, Jul. 1992, pp. 4517–4523.

Schuster, et al., *Journal of Bacteriology*, Nov. 1990, pp. 6499–6505.

*Primary Examiner*—Anthony C. Caputa
*Assistant Examiner*—Mark Navarro
*Attorney, Agent, or Firm*—Thomas D. Webster; David E. Boone

[57] ABSTRACT

The invention provides isolated nucleic acid compounds encoding a novel high molecular weight PBP of *Streptococcus pneumoniae*. Also provided are vectors and transformed heterologous host cells for expressing the PBP and a method for identifying compounds that bind and/or inhibit the enzymatic activity of the PBP.

17 Claims, 1 Drawing Sheet

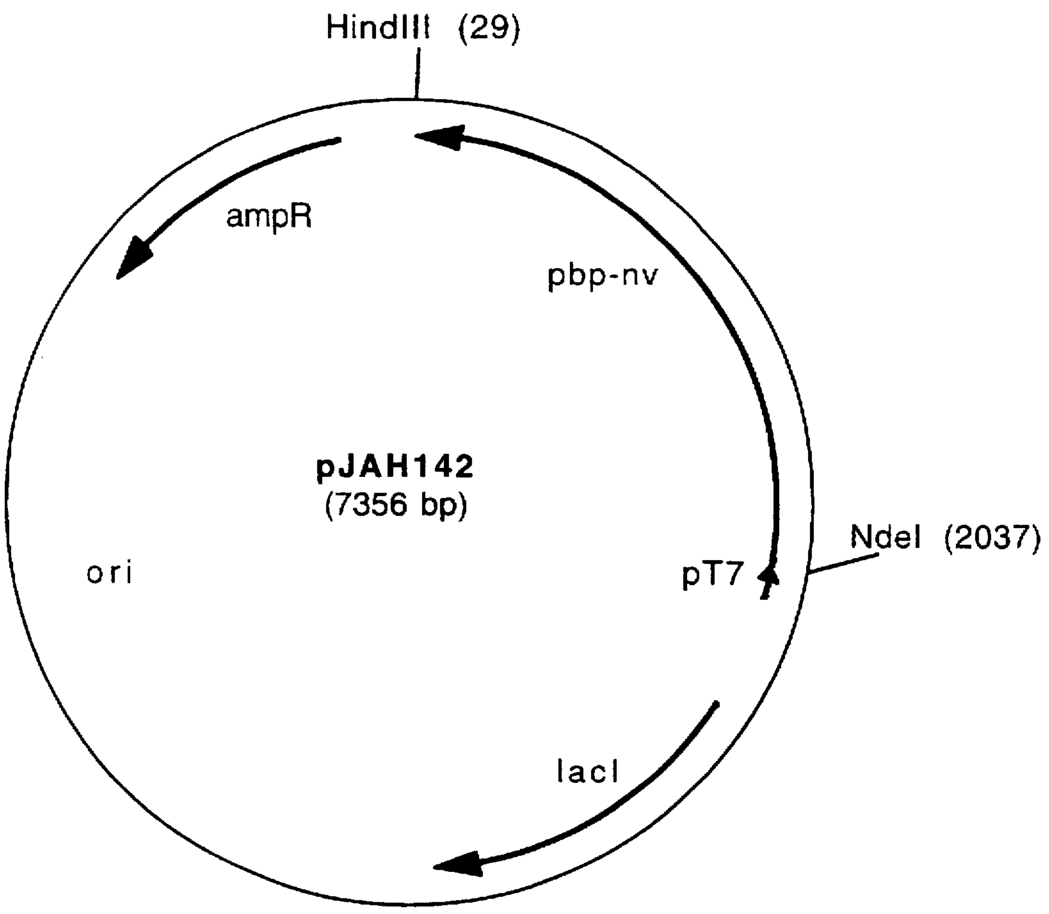
HindIII (29)
ampR
pbp-nv
pJAH142
(7356 bp)
NdeI (2037)
ori
pT7
lacI

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 2193 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION: 1..2193

( x i ) SEQUENCE DESCRIPTION: SEQ ID NO:1:

```
ATG AAA TTA GAT AAA TTA TTT GAG AAA TTT CTT TCT CTT TTT AAA AAA      48
Met Lys Leu Asp Lys Leu Phe Glu Lys Phe Leu Ser Leu Phe Lys Lys
  1               5                  10                  15

GAA ACA AGT GAA CTA GAG GAC TCT GAT TCT ACT ATC TTA CGT CGC TCT      96
Glu Thr Ser Glu Leu Glu Asp Ser Asp Ser Thr Ile Leu Arg Arg Ser
             20                  25                  30

CGT AGT GAT CGA AAA AAA TTA GCC CAA GTA GGT CCG ATT CGA AAA TTC     144
Arg Ser Asp Arg Lys Lys Leu Ala Gln Val Gly Pro Ile Arg Lys Phe
         35                  40                  45
```

-continued

```
TGG CGT CGT TAT CAT CTA ACA AAG ATT ATC CTT ATA CTA GGT TTG AGT    192
Trp Arg Arg Tyr His Leu Thr Lys Ile Ile Leu Ile Leu Gly Leu Ser
     50                  55                  60

GCA GGC TTG CTA GTT GGA ATC TAT TTG TTT GCT GTA GCC AAG TCG ACC    240
Ala Gly Leu Leu Val Gly Ile Tyr Leu Phe Ala Val Ala Lys Ser Thr
 65                  70                  75                  80

AAT GTC AAT GAT TTG CAA AAT GCC TTG AAA ACT CGG ACT CTT ATT TTT    288
Asn Val Asn Asp Leu Gln Asn Ala Leu Lys Thr Arg Thr Leu Ile Phe
                 85                  90                  95

GAC CGT GAA GAA AAA GAG GCT GGT GCC TTG TCT GGT CAA AAG GGA ACC    336
Asp Arg Glu Glu Lys Glu Ala Gly Ala Leu Ser Gly Gln Lys Gly Thr
            100                 105                 110

TAT GTT GAG CTG ACT GAC ATC AGT AAA AAC TTG CAG AAT GCT GTT ATT    384
Tyr Val Glu Leu Thr Asp Ile Ser Lys Asn Leu Gln Asn Ala Val Ile
        115                 120                 125

GCG ACA GAA GAC CGT TCT TTC TAT AAA AAT GAC GGG ATT AAC TAT GGC    432
Ala Thr Glu Asp Arg Ser Phe Tyr Lys Asn Asp Gly Ile Asn Tyr Gly
    130                 135                 140

CGT TTC TTC TTG GCT ATT GTC ACT GCT GGA CGT TCA GGT GGT GGC TCT    480
Arg Phe Phe Leu Ala Ile Val Thr Ala Gly Arg Ser Gly Gly Gly Ser
145                 150                 155                 160

ACC ATT ACC CAA CAG CTG GCT AAA AAC GCC TAT TTA TCG CAG GAT CAA    528
Thr Ile Thr Gln Gln Leu Ala Lys Asn Ala Tyr Leu Ser Gln Asp Gln
            165                 170                 175

ACT GTT GAG AGA AAA GCG AAA GAA TTT TTC CTT GCC TTA GAA TTA AGC    576
Thr Val Glu Arg Lys Ala Lys Glu Phe Phe Leu Ala Leu Glu Leu Ser
            180                 185                 190

AAA AAA TAT AGT AAG GAG CAA ATT CTA ACC ATG TAC CTT AAC AAC GCT    624
Lys Lys Tyr Ser Lys Glu Gln Ile Leu Thr Met Tyr Leu Asn Asn Ala
        195                 200                 205

TAT TTT GGA AAT GGT GTG TGG GGT GTA GAA GAT GCG AGT AAG AAA TAC    672
Tyr Phe Gly Asn Gly Val Trp Gly Val Glu Asp Ala Ser Lys Lys Tyr
    210                 215                 220

TTT GGA GTT TCT GCA TCA GAA GTG AGT CTG GAT CAA GCT GCG ACT CTG    720
Phe Gly Val Ser Ala Ser Glu Val Ser Leu Asp Gln Ala Ala Thr Leu
225                 230                 235                 240

GCA GGG ATG CTC AAG GGG CCG GAA CTG TAT AAT CCC TTG AAT TCC GTA    768
Ala Gly Met Leu Lys Gly Pro Glu Leu Tyr Asn Pro Leu Asn Ser Val
                245                 250                 255

GAA GAT TCT ACT AAT CGG CGC GAT ACT GTC TTG CAG AAT ATG GTT GCA    816
Glu Asp Ser Thr Asn Arg Arg Asp Thr Val Leu Gln Asn Met Val Ala
            260                 265                 270

GCA GGA TAT ATT GAT AAA AAC CAA GAA ACC GAA GCT GCT GAA GTT GAT    864
Ala Gly Tyr Ile Asp Lys Asn Gln Glu Thr Glu Ala Ala Glu Val Asp
        275                 280                 285

ATG ACT TCG CAA TTG CAC GAT AAG TAT GAA GGA AAA ATC TCA GAT TAC    912
Met Thr Ser Gln Leu His Asp Lys Tyr Glu Gly Lys Ile Ser Asp Tyr
    290                 295                 300

CGT TAC CCC TCT TAT TTT GAT GCG GTG GTT AAT GAA GCT GTT TCC AAG    960
Arg Tyr Pro Ser Tyr Phe Asp Ala Val Val Asn Glu Ala Val Ser Lys
305                 310                 315                 320

TAT AAT CTA ACA GAG GAA GAG ATT GTC AAT AAT GGC TAC CGC ATT TAC   1008
Tyr Asn Leu Thr Glu Glu Glu Ile Val Asn Asn Gly Tyr Arg Ile Tyr
                325                 330                 335

ACA GAG CTG GAC CAA AAC TAC CAA GCA AAT ATG CAG ATT GTT TAT GAA   1056
Thr Glu Leu Asp Gln Asn Tyr Gln Ala Asn Met Gln Ile Val Tyr Glu
            340                 345                 350

AAC ACA TCG CTA TTT CCG AGG GCA GAG GAT GGA ACG TTT GCT CAA TCA   1104
Asn Thr Ser Leu Phe Pro Arg Ala Glu Asp Gly Thr Phe Ala Gln Ser
        355                 360                 365
```

-continued

```
GGA AGT GTA GCT CTC GAA CCG AAA ACA GGG GGA GTT CGT GGA GTT GTC  1152
Gly Ser Val Ala Leu Glu Pro Lys Thr Gly Gly Val Arg Gly Val Val
    370                 375                 380

GGT CAA GTT GCT GAC AAT GAT AAA ACT GGA TTC CGG AAT TTC AAC TAT  1200
Gly Gln Val Ala Asp Asn Asp Lys Thr Gly Phe Arg Asn Phe Asn Tyr
385                 390                 395                 400

GCA ACC CAA TCA AAG CGT AGT CCT GGT TCT ACA ATT AAG CCT TTA GTT  1248
Ala Thr Gln Ser Lys Arg Ser Pro Gly Ser Thr Ile Lys Pro Leu Val
                405                 410                 415

GTT TAT ACA CCA GCA GTT GAA GCA GGC TGG GCT TTG AAT AAG CAG TTG  1296
Val Tyr Thr Pro Ala Val Glu Ala Gly Trp Ala Leu Asn Lys Gln Leu
            420                 425                 430

GAT AAC CAT ACC ATG CAG TAT GAT AGC TAT AAG GTT GAT AAC TAT GCA  1344
Asp Asn His Thr Met Gln Tyr Asp Ser Tyr Lys Val Asp Asn Tyr Ala
        435                 440                 445

GGG ATC AAA ACA AGT CGA GAA GTT CCT ATG TAT CAA TCC TTG GCA GAA  1392
Gly Ile Lys Thr Ser Arg Glu Val Pro Met Tyr Gln Ser Leu Ala Glu
    450                 455                 460

TCG CTT AAT CTA CCT GCT GTT GCC ACT GTT AAT GAT TTG GGT GTT GAC  1440
Ser Leu Asn Leu Pro Ala Val Ala Thr Val Asn Asp Leu Gly Val Asp
465                 470                 475                 480

AAG GCT TTT GAG GCA GGC GAA AAA TTC GGA CTC AAC ATG GAA AAG GTC  1488
Lys Ala Phe Glu Ala Gly Glu Lys Phe Gly Leu Asn Met Glu Lys Val
                485                 490                 495

GAC CGT GTT CTT GGT GTC GCC TTG GGA AGC GGT GTT GAA ACC AAC CCT  1536
Asp Arg Val Leu Gly Val Ala Leu Gly Ser Gly Val Glu Thr Asn Pro
            500                 505                 510

CTT CAA ATG GCT CAA GCA TAC GCT GCC TTT GCA AAT GAA GGT TTA ATG  1584
Leu Gln Met Ala Gln Ala Tyr Ala Ala Phe Ala Asn Glu Gly Leu Met
        515                 520                 525

CCT GAA GCT CAT TTT ATT AGT AGA ATT GAA AAT GCT AGT GGA CAA GTT  1632
Pro Glu Ala His Phe Ile Ser Arg Ile Glu Asn Ala Ser Gly Gln Val
    530                 535                 540

ATT GCG AGT CAT AAA AAT TCA CAA AAA CGG GTG ATT GAT AAG TCT GTA  1680
Ile Ala Ser His Lys Asn Ser Gln Lys Arg Val Ile Asp Lys Ser Val
545                 550                 555                 560

GCT GAC AAG ATG ACC AGT ATG ATG TTG GGG ACT TTC ACC AAC GGT ACC  1728
Ala Asp Lys Met Thr Ser Met Met Leu Gly Thr Phe Thr Asn Gly Thr
                565                 570                 575

GGT ATT AGT TCA TCG CCT GCA GAC TAT GTC ATG GCA GGG AAA ACT GGA  1776
Gly Ile Ser Ser Ser Pro Ala Asp Tyr Val Met Ala Gly Lys Thr Gly
            580                 585                 590

ACA ACT GAA GCA GTT TTC AAT CCG GAG TAC ACA AGT GAC CAG TGG GTA  1824
Thr Thr Glu Ala Val Phe Asn Pro Glu Tyr Thr Ser Asp Gln Trp Val
        595                 600                 605

ATT GGT TAT ACT CCG GAT GTA GTG ATT AGC CAC TGG CTT GGC TTT CCG  1872
Ile Gly Tyr Thr Pro Asp Val Val Ile Ser His Trp Leu Gly Phe Pro
    610                 615                 620

ACC ACT GAT GAA AAT CAC TAT CTA GCT GGC TCT ACT TCA AAC GGT GCA  1920
Thr Thr Asp Glu Asn His Tyr Leu Ala Gly Ser Thr Ser Asn Gly Ala
625                 630                 635                 640

GCT CAT GTC TTT AGA AAC ATT GCC AAT ACT ATT TTA CCT TAT ACG CCA  1968
Ala His Val Phe Arg Asn Ile Ala Asn Thr Ile Leu Pro Tyr Thr Pro
                645                 650                 655

GGA AGT ACC TTT ACG GTT GAA AAT GCT TAT AAG CAA AAT GGA ATT GCA  2016
Gly Ser Thr Phe Thr Val Glu Asn Ala Tyr Lys Gln Asn Gly Ile Ala
            660                 665                 670

CCA GCC AAT ACA AAA AGA CAA GTA CAA ACC AAT GAT AAT AGC CAG ACA  2064
Pro Ala Asn Thr Lys Arg Gln Val Gln Thr Asn Asp Asn Ser Gln Thr
        675                 680                 685
```

-continued

```
GAT GAT AAT TTG TCT GAT ATT CGA GGG CGT GCG CAA AGT CTA GTA GAT      2112
Asp Asp Asn Leu Ser Asp Ile Arg Gly Arg Ala Gln Ser Leu Val Asp
    690                 695                 700

GAG GCT AGC CGG GCT ATC TCA GAT GCG AAG ATT AAG GAA AAG GCT CAA      2160
Glu Ala Ser Arg Ala Ile Ser Asp Ala Lys Ile Lys Glu Lys Ala Gln
705                 710                 715                 720

ACA ATA TGG GAT TCG ATA GTC AAT CTA TTT CGC                          2193
Thr Ile Trp Asp Ser Ile Val Asn Leu Phe Arg
                725                 730
```

( 2 ) INFORMATION FOR SEQ ID NO:2:

( i ) SEQUENCE CHARACTERISTICS:
( A ) LENGTH: 731 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Lys Leu Asp Lys Leu Phe Glu Lys Phe Leu Ser Leu Phe Lys Lys
  1               5                  10                  15

Glu Thr Ser Glu Leu Glu Asp Ser Asp Ser Thr Ile Leu Arg Arg Ser
             20                  25                  30

Arg Ser Asp Arg Lys Lys Leu Ala Gln Val Gly Pro Ile Arg Lys Phe
         35                  40                  45

Trp Arg Arg Tyr His Leu Thr Lys Ile Ile Leu Ile Leu Gly Leu Ser
     50                  55                  60

Ala Gly Leu Leu Val Gly Ile Tyr Leu Phe Ala Val Ala Lys Ser Thr
 65                  70                  75                  80

Asn Val Asn Asp Leu Gln Asn Ala Leu Lys Thr Arg Thr Leu Ile Phe
                 85                  90                  95

Asp Arg Glu Glu Lys Glu Ala Gly Ala Leu Ser Gly Gln Lys Gly Thr
            100                 105                 110

Tyr Val Glu Leu Thr Asp Ile Ser Lys Asn Leu Gln Asn Ala Val Ile
        115                 120                 125

Ala Thr Glu Asp Arg Ser Phe Tyr Lys Asn Asp Gly Ile Asn Tyr Gly
    130                 135                 140

Arg Phe Phe Leu Ala Ile Val Thr Ala Gly Arg Ser Gly Gly Gly Ser
145                 150                 155                 160

Thr Ile Thr Gln Gln Leu Ala Lys Asn Ala Tyr Leu Ser Gln Asp Gln
                165                 170                 175

Thr Val Glu Arg Lys Ala Lys Glu Phe Phe Leu Ala Leu Glu Leu Ser
            180                 185                 190

Lys Lys Tyr Ser Lys Glu Gln Ile Leu Thr Met Tyr Leu Asn Asn Ala
        195                 200                 205

Tyr Phe Gly Asn Gly Val Trp Gly Val Glu Asp Ala Ser Lys Lys Tyr
    210                 215                 220

Phe Gly Val Ser Ala Ser Glu Val Ser Leu Asp Gln Ala Ala Thr Leu
225                 230                 235                 240

Ala Gly Met Leu Lys Gly Pro Glu Leu Tyr Asn Pro Leu Asn Ser Val
                245                 250                 255

Glu Asp Ser Thr Asn Arg Arg Asp Thr Val Leu Gln Asn Met Val Ala
            260                 265                 270

Ala Gly Tyr Ile Asp Lys Asn Gln Glu Thr Glu Ala Ala Glu Val Asp
        275                 280                 285

Met Thr Ser Gln Leu His Asp Lys Tyr Glu Gly Lys Ile Ser Asp Tyr
    290                 295                 300
```

-continued

| | | | | | | | | | | | | | | | |
|---|---|---|---|---|---|---|---|---|---|---|---|---|---|---|---|
| Arg | Tyr | Pro | Ser | Tyr | Phe | Asp | Ala | Val | Val | Asn | Glu | Ala | Val | Ser | Lys |
| 305 | | | | | 310 | | | | | 315 | | | | | 320 |
| Tyr | Asn | Leu | Thr | Glu | Glu | Glu | Ile | Val | Asn | Asn | Gly | Tyr | Arg | Ile | Tyr |
| | | | | 325 | | | | | 330 | | | | | 335 | |
| Thr | Glu | Leu | Asp | Gln | Asn | Tyr | Gln | Ala | Asn | Met | Gln | Ile | Val | Tyr | Glu |
| | | | 340 | | | | | 345 | | | | | 350 | | |
| Asn | Thr | Ser | Leu | Phe | Pro | Arg | Ala | Glu | Asp | Gly | Thr | Phe | Ala | Gln | Ser |
| | | 355 | | | | | 360 | | | | | 365 | | | |
| Gly | Ser | Val | Ala | Leu | Glu | Pro | Lys | Thr | Gly | Gly | Val | Arg | Gly | Val | Val |
| | 370 | | | | | 375 | | | | | 380 | | | | |
| Gly | Gln | Val | Ala | Asp | Asn | Asp | Lys | Thr | Gly | Phe | Arg | Asn | Phe | Asn | Tyr |
| 385 | | | | | 390 | | | | | 395 | | | | | 400 |
| Ala | Thr | Gln | Ser | Lys | Arg | Ser | Pro | Gly | Ser | Thr | Ile | Lys | Pro | Leu | Val |
| | | | | 405 | | | | | 410 | | | | | 415 | |
| Val | Tyr | Thr | Pro | Ala | Val | Glu | Ala | Gly | Trp | Ala | Leu | Asn | Lys | Gln | Leu |
| | | | 420 | | | | | 425 | | | | | 430 | | |
| Asp | Asn | His | Thr | Met | Gln | Tyr | Asp | Ser | Tyr | Lys | Val | Asp | Asn | Tyr | Ala |
| | | 435 | | | | | 440 | | | | | 445 | | | |
| Gly | Ile | Lys | Thr | Ser | Arg | Glu | Val | Pro | Met | Tyr | Gln | Ser | Leu | Ala | Glu |
| | 450 | | | | | 455 | | | | | 460 | | | | |
| Ser | Leu | Asn | Leu | Pro | Ala | Val | Ala | Thr | Val | Asn | Asp | Leu | Gly | Val | Asp |
| 465 | | | | | 470 | | | | | 475 | | | | | 480 |
| Lys | Ala | Phe | Glu | Ala | Gly | Glu | Lys | Phe | Gly | Leu | Asn | Met | Glu | Lys | Val |
| | | | | 485 | | | | | 490 | | | | | 495 | |
| Asp | Arg | Val | Leu | Gly | Val | Ala | Leu | Gly | Ser | Gly | Val | Glu | Thr | Asn | Pro |
| | | | 500 | | | | | 505 | | | | | 510 | | |
| Leu | Gln | Met | Ala | Gln | Ala | Tyr | Ala | Ala | Phe | Ala | Asn | Glu | Gly | Leu | Met |
| | | 515 | | | | | 520 | | | | | 525 | | | |
| Pro | Glu | Ala | His | Phe | Ile | Ser | Arg | Ile | Glu | Asn | Ala | Ser | Gly | Gln | Val |
| | 530 | | | | | 535 | | | | | 540 | | | | |
| Ile | Ala | Ser | His | Lys | Asn | Ser | Gln | Lys | Arg | Val | Ile | Asp | Lys | Ser | Val |
| 545 | | | | | 550 | | | | | 555 | | | | | 560 |
| Ala | Asp | Lys | Met | Thr | Ser | Met | Met | Leu | Gly | Thr | Phe | Thr | Asn | Gly | Thr |
| | | | | 565 | | | | | 570 | | | | | 575 | |
| Gly | Ile | Ser | Ser | Ser | Pro | Ala | Asp | Tyr | Val | Met | Ala | Gly | Lys | Thr | Gly |
| | | | 580 | | | | | 585 | | | | | 590 | | |
| Thr | Thr | Glu | Ala | Val | Phe | Asn | Pro | Glu | Tyr | Thr | Ser | Asp | Gln | Trp | Val |
| | | 595 | | | | | 600 | | | | | 605 | | | |
| Ile | Gly | Tyr | Thr | Pro | Asp | Val | Val | Ile | Ser | His | Trp | Leu | Gly | Phe | Pro |
| | 610 | | | | | 615 | | | | | 620 | | | | |
| Thr | Thr | Asp | Glu | Asn | His | Tyr | Leu | Ala | Gly | Ser | Thr | Ser | Asn | Gly | Ala |
| 625 | | | | | 630 | | | | | 635 | | | | | 640 |
| Ala | His | Val | Phe | Arg | Asn | Ile | Ala | Asn | Thr | Ile | Leu | Pro | Tyr | Thr | Pro |
| | | | | 645 | | | | | 650 | | | | | 655 | |
| Gly | Ser | Thr | Phe | Thr | Val | Glu | Asn | Ala | Tyr | Lys | Gln | Asn | Gly | Ile | Ala |
| | | | 660 | | | | | 665 | | | | | 670 | | |
| Pro | Ala | Asn | Thr | Lys | Arg | Gln | Val | Gln | Thr | Asn | Asp | Asn | Ser | Gln | Thr |
| | | 675 | | | | | 680 | | | | | 685 | | | |
| Asp | Asp | Asn | Leu | Ser | Asp | Ile | Arg | Gly | Arg | Ala | Gln | Ser | Leu | Val | Asp |
| | 690 | | | | | 695 | | | | | 700 | | | | |
| Glu | Ala | Ser | Arg | Ala | Ile | Ser | Asp | Ala | Lys | Ile | Lys | Glu | Lys | Ala | Gln |
| 705 | | | | | 710 | | | | | 715 | | | | | 720 |

-continued

Thr Ile Trp Asp Ser Ile Val Asn Leu Phe Arg
725 730

( 2 ) INFORMATION FOR SEQ ID NO:3:

( i ) SEQUENCE CHARACTERISTICS:
( A ) LENGTH: 2193 base pairs
( B ) TYPE: nucleic acid
( C ) STRANDEDNESS: single
( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:3:

AUGAAAUUAG AUAAAUUAUU UGAGAAAUUU CUUUCUCUUU UUAAAAAAGA AACAAGUGAA 60
CUAGAGGACU CUGAUUCUAC UAUCUUACGU CGCUCUCGUA GUGAUCGAAA AAAAUUAGCC 120
CAAGUAGGUC CGAUUCGAAA AUUCUGGCGU CGUUAUCAUC UAACAAAGAU UAUCCUUAUA 180
CUAGGUUUGA GUGCAGGCUU GCUAGUUGGA AUCUAUUUGU UUGCUGUAGC CAAGUCGACC 240
AAUGUCAAUG AUUUGCAAAA UGCCUUGAAA ACUCGGACUC UUAUUUUUGA CCGUGAAGAA 300
AAAGAGGCUG GUGCCUUGUC UGGUCAAAAG GGAACCUAUG UUGAGCUGAC UGACAUCAGU 360
AAAAACUUGC AGAAUGCUGU UAUUGCGACA GAAGACCGUU CUUUCUAUAA AAAUGACGGG 420
AUUAACUAUG GCCGUUUCUU CUUGGCUAUU GUCACUGCUG GACGUUCAGG UGGUGGCUCU 480
ACCAUUACCC AACAGCUGGC UAAAAACGCC UAUUUAUCGC AGGAUCAAAC UGUUGAGAGA 540
AAAGCGAAAG AAUUUUUCCU UGCCUUAGAA UUAAGCAAAA AAUAUAGUAA GGAGCAAAUU 600
CUAACCAUGU ACCUUAACAA CGCUUAUUUU GGAAAUGGUG UGUGGGGUGU AGAAGAUGCG 660
AGUAAGAAAU ACUUUGGAGU UUCUGCAUCA GAAGUGAGUC UGGAUCAAGC UGCGACUCUG 720
GCAGGGAUGC UCAAGGGGCC GGAACUGUAU AAUCCCUUGA AUUCCGUAGA AGAUUCUACU 780
AAUCGGCGCG AUACUGUCUU GCAGAAUAUG GUUGCAGCAG GAUAUAUUGA UAAAAACCAA 840
GAAACCGAAG CUGCUGAAGU UGAUAUGACU UCGCAAUUGC ACGAUAAGUA UGAAGGAAAA 900
AUCUCAGAUU ACCGUUACCC CUCUUAUUUU GAUGCGGUGG UUAAUGAAGC UGUUUCCAAG 960
UAUAAUCUAA CAGAGGAAGA GAUUGUCAAU AAUGGCUACC GCAUUUACAC AGAGCUGGAC 1020
CAAAACUACC AAGCAAAUAU GCAGAUUGUU UAUGAAAACA CAUCGCUAUU UCCGAGGGCA 1080
GAGGAUGGAA CGUUUGCUCA AUCAGGAAGU GUAGCUCUCG AACCGAAAAC AGGGGGAGUU 1140
CGUGGAGUUG UCGGUCAAGU UGCUGACAAU GAUAAAACUG GAUUCCGGAA UUUCAACUAU 1200
GCAACCCAAU CAAAGCGUAG UCCUGGUUCU ACAAUUAAGC CUUUAGUUGU UUAUACACCA 1260
GCAGUUGAAG CAGGCUGGGC UUUGAAUAAG CAGUUGGAUA ACCAUACCAU GCAGUAUGAU 1320
AGCUAUAAGG UUGAUAACUA UGCAGGGAUC AAAACAAGUC GAGAAGUUCC UAUGUAUCAA 1380
UCCUUGGCAG AAUCGCUUAA UCUACCUGCU GUUGCCACUG UUAAUGAUUU GGGUGUUGAC 1440
AAGGCUUUUG AGGCAGGCGA AAAAUUCGGA CUCAACAUGG AAAAGGUCGA CCGUGUUCUU 1500
GGUGUCGCCU UGGGAAGCGG UGUUGAAACC AACCCUCUUC AAAUGGCUCA AGCAUACGCU 1560
GCCUUUGCAA AUGAAGGUUU AAUGCCUGAA GCUCAUUUUA UUAGUAGAAU UGAAAAUGCU 1620
AGUGGACAAG UUAUUGCGAG UCAUAAAAAU UCACAAAAAC GGGUGAUUGA UAAGUCUGUA 1680
GCUGACAAGA UGACCAGUAU GAUGUUGGGG ACUUUCACCA ACGGUACCGG UAUUAGUUCA 1740
UCGCCUGCAG ACUAUGUCAU GGCAGGGAAA ACUGGAACAA CUGAAGCAGU UUUCAAUCCG 1800

-continued

| | | | | | | |
|---|---|---|---|---|---|---|
| GAGUACACAA | GUGACCAGUG | GGUAAUUGGU | UAUACUCCGG | AUGUAGUGAU | UAGCCACUGG | 1860 |
| CUUGGCUUUC | CGACCACUGA | UGAAAAUCAC | UAUCUAGCUG | GCUCUACUUC | AAACGGUGCA | 1920 |
| GCUCAUGUCU | UUAGAAACAU | UGCCAAUACU | AUUUUACCUU | AUACGCCAGG | AAGUACCUUU | 1980 |
| ACGGUUGAAA | AUGCUUAUAA | GCAAAAUGGA | AUUGCACCAG | CCAAUACAAA | AAGACAAGUA | 2040 |
| CAAACCAAUG | AUAAUAGCCA | GACAGAUGAU | AAUUUGUCUG | AUAUUCGAGG | GCGUGCGCAA | 2100 |
| AGUCUAGUAG | AUGAGGCUAG | CCGGGCUAUC | UCAGAUGCGA | AGAUUAAGGA | AAAGGCUCAA | 2160 |
| ACAAUAUGGG | AUUCGAUAGU | CAAUCUAUUU | CGC | | | 2193 |

DNA ENCODING A NOVEL PENICILLIN BINDING PROTEIN FROM STREPTOCOCCUS PNEUMONIAE

BACKGROUND OF THE INVENTION

This invention relates to recombinant DNA technology. In particular the invention pertains to the cloning of a gene, pbp-nv, encoding a novel high molecular weight penicillin binding protein (PBP), PBP-Nv, from *Streptococcus pneumoniae* and the use of said gene and its encoded protein in a screen for new inhibitors of bacterial cell wall biosynthesis.

The emergence of antibiotic resistance in common pathogenic bacterial species has justifiably alarmed the medical and research communities. The emergence and rapid spread of beta-lactam resistance in *Streptococcus pneumoniae* has been particularly problematic. This organism is responsible for many respiratory tract infections, and resistance to beta-lactam drugs has been attributed to a modification of one or more of the penicillin-binding proteins (PBPs). Furthermore, penicillin-resistant *Streptococcus pneumoniae* are frequently resistant to other commonly used antibiotics, such as erythromycin. These multi-drug resistant (MDR) organisms are a real threat to humans, particularly children and the elderly.

Increasingly, the only drug that can be used to treat infections with MDR organisms is vancomycin, and there is considerable concern that the bacteria could also develop resistance to vancomycin.

The PBPs are involved in bacterial cell wall synthesis. The cell wall comprises a peptidoglycan layer which provides mechanical rigidity for the bacterium. The peptidoglycan layer is composed of a sugar backbone (alternating residues of N-acetylglucosamine and N-acetylmuramic acid) attached to a pentapeptide (also referred to as "stem peptide") containing D and L amino acid residues. In the formation of the mature peptidoglycan, a lipid-linked disaccharide-pentapeptide is translocated across the cytoplasmic membrane, exposing the pentapeptide sidechains to the cell surface. Transglycosylation of the sugar residues then leads to polymerization of the backbone sugar residues. Further stabilization of the nascent peptidoglycan occurs by a transpeptidation enzymatic reaction that crosslinks adjacent pentapeptide moieties. The high molecular weight PBPs catalyze these final steps in peptidoglycan synthesis. Without the crosslinking step the peptidoglycan structure is severely weakened and susceptible to degradation. Indeed, the crosslinking step constitutes the target of action for antibiotic compounds such as penicillin and other beta-lactam drugs.

When effective as antibiotic agents, beta-lactam drugs interact with PBPs to form an acyl-enzyme intermediate. This intermediate is resistant to hydrolysis. Mechanistically, beta-lactam drugs act as irreversible inhibitors. Resistance to beta-lactam drugs in *Streptococcus pneumoniae* arises through mutation events such that one or more low-affinity "mosaic" PBPs replace a wild-type PBP. The molecular basis of resistance has in a few cases been correlated with specific mutations within a PBP gene. The discovery of new antibacterial compounds against the transpeptidase domain of PBP-Nv or to an unexploited target (e.g. the transglycosylase domain) would be particularly useful against *Streptococcus pneumoniae* infections.

SUMMARY OF THE INVENTION

The present invention is designed to meet the aforementioned need and provides, inter alia, isolated nucleic acid molecules that encode a novel PBP from *Streptococcus pneumoniae*. The invention also provides protein products encoded by the gene, in substantially purified form.

Having the cloned pbp-nv gene of *Streptococcus pneumoniae* enables the production of recombinant PBP-Nv protein and derivatives thereof for the implementation of assays and screens to identify new inhibitory compounds targeted at the peptidoglycan biosynthetic pathway.

In one embodiment the present invention relates to isolated gene pbp-nv that encodes novel *Streptococcus pneumoniae* PBP, PBP-Nv, said gene comprising the nucleotide sequence identified as SEQ ID NO. 1.

In another embodiment the present invention relates to a novel protein molecule, PBP-Nv, wherein said protein molecule comprises the sequence identified as SEQ ID NO. 2.

In another embodiment, the present invention relates to a soluble form of PBP-Nv (designated PBP-$Nv^S$) wherein PBP-$Nv^S$ comprises amino acid residues 78 through 731, inclusive, of SEQ ID NO.2.

In a further embodiment the present invention relates to a ribonucleic acid molecule encoding PBP-Nv protein, said ribonucleic acid molecule comprising the sequence identified as SEQ ID NO. 3:

In yet another embodiment, the present invention relates to a recombinant DNA vector that incorporates the *Streptococcus pneumoniae* pbp-nv gene in operable linkage to gene expression sequences enabling said PBP gene to be transcribed and translated in a host cell.

In still another embodiment the present invention relates to homologous or heterologous host cells that have been transformed or transfected with a vector carrying the cloned pbp-nv gene from *Streptococcus pneumoniae* such that said gene is expressed in the host cell.

In a still further embodiment, the present invention relates to a method for identifying compounds that bind the *Streptococcus pneumoniae* PBP-Nv protein or fragment thereof.

DESCRIPTION OF THE DRAWINGS

FIGURE. Plasmid JAH142, useful for high level expression of the *Streptococcus pneumoniae* pbp-$nv^S$ gene of the present invention in the heterologous procaryotic host cell *Eschericia coli*.

DEFINITIONS

"PBP" refers generically to a penicillin binding protein.

"PBP-Nv" refers to the novel high molecular weight PBP from *Streptococcus pneumoniae* that is the subject of this invention and which is specified by SEQ ID NO.2.

"PBP-$Nv^S$" refers to a soluble form of PBP-Nv wherein the membrane spanning region and the cytoplasmic region of PBP-Nv have been removed, leaving amino acid residues 78 through 731 of SEQ ID NO.2.

"pbp-nv" refers to the *Streptococcus pneumoniae* genomic sequence encoding PBP-Nv.

"pbp-$nv^S$" refers to a portion of pbp-nv that encodes PBP-$Nv^S$ comprising nucleotide residues 232 through 2193 of SEQ ID NO.1.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art.

Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

"Functional domain" refers to a region of a protein having one or more distinct biological functions, for example, enzymatic activity, transmembrane anchoring, DNA binding, etc. A functional domain comprises a sequence of amino acids, the length of which and the identity of amino acid residues therein, may or may not be critical to function.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound that hybridizes with another nucleic acid compound.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon, for example, the degree of complementarity, the stringency of hybridization, and the length of hybridizing strands.

The term "stringency" refers to hybridization conditions. High stringency conditions disfavor non-homologous base-pairing. Low stringency conditions have the opposite effect. Stringency may be altered, for example, by temperature and salt concentration.

"Transglycosylation" refers to an enzymatic reaction catalyzed by a high molecular weight PBP in which the sugar residues of lipid-linked disaccharide pentapeptide molecules are polymerized during the formation of the peptidoglycan structure of the bacterial cell wall.

"Transpeptidation" refers to an enzymatic reaction catalyzed by a high molecular weight PBP in which the pentapeptide sidechains of lipid-linked disaccharide pentapeptde molecules are cross-linked during the formation of the peptidoglycan structure of the bacterial cell wall.

DETAILED DESCRIPTION

The pbp-nv gene (SEQ ID NO.1) of the present invention encodes a novel high molecular weight PBP of *Streptococcus pneumoniae* (SEQ ID NO. 2). The pbp-nv gene disclosed herein comprises a DNA sequence of 2193 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product. All such substitutions are intended to be within the scope of the invention.

The PBP-Nv protein defined by SEQ ID NO.2 comprises a membrane-bound protein having several functional domains. At the amino terminal end, amino acid residues from about 1 through 56 of SEQ ID NO.2 define a cytoplasmic domain. The middle portion of the molecule from about amino acid residues 57 through 77 of SEQ ID NO.2, comprises a trans-membrane region. At the carboxy terminal end of the molecule, which extends into the extracellular environment, amino acid residues from about 78 through 731 of SEQ ID NO.2 comprise a functional domain, wherein resides the transpeptidation (viz. penicillin-binding) and transglycosylase activities.

The PBP-Nv protein may be modified by deletion of one or more functional domains. For example, the amino terminal domain and trans-membrane domains may be deleted without a loss of function at the carboxy terminal end (viz. binding of penicillin and transglycosylase activity). A deleted form of the PBP-Nv protein lacking the amino terminal and transmembrane regions results in a soluble form of the protein, designated PBP-$Nv^S$.

Gene Isolation Procedures

Those skilled in the art will recogize that the gene of the present invention may be obtained by a plurality of applicable genetic and recombinant DNA techniques including, for example, polymerase chain reaction (PCR) amplification, or de novo DNA synthesis.(See e.g., J.Sambrook et al. *Molecular Cloning,* 2d Ed. Chap. 14 (1989)).

Methods for constructing gene libraries in a suitable vector such as a plasmid or phage for propagation in procaryotic or eucaryotic cells are well known to those skilled in the art. [See e.g. J.Sambrook et al. Supra]. Suitable cloning vectors are widely available.

Skilled artisans will recognize that the pbp-nv gene of *Streptococcus pneumoniae* comprising the present invention or fragment thereof could be isolated by PCR amplification of *Streptococcus pneumoniae* genomic DNA or cDNA using oligonucleotide primers targeted to any suitable region of SEQ ID NO.1. Methods for PCR amplification are widely known in the art. See e.g. *PCR Protocols: A Guide to*

*Method and Application*, Ed. M. Innis et al., Academic Press (1990). The amplification reaction comprises genomic DNA, suitable enzymes, primers, and buffers, and is conveniently carried out in a DNA Thermal Cycler (Perkin Elmer Cetus, Norwalk, Conn). A positive result is determined by detecting an appropriately-sized DNA fragment following agarose gel electrophoresis.

Protein Production Methods

One embodiment of the present invention relates to the substantially purified protein or fragments thereof encoded by the gene disclosed herein (SEQ ID NO.1).

Skilled artisans will recognize that the protein of the present invention can be synthesized by any number of to different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, New York, 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The protein of the present invention can also be produced by recombinant DNA methods using the cloned gene of *Streptococcus pneumoniae* disclosed herein. Recombinant methods are preferred if a high yield is desired. Expression of said cloned gene can be carried out in a variety of suitable host cells well known to those skilled in the art. In a recombinant method the pbp-nv or pbp-$nv^S$ gene is introduced into a host cell by any suitable means, well known to those skilled in the art. While chromosomal integration of the cloned PBP gene is within the scope of the present invention, it is preferred that the gene be cloned into a suitable extra-chromosomally maintained expression vector so that the coding region of the gene is operably linked to a constitutive or inducible promoter.

The basic steps in the recombinant production of PBP-Nv or PBP-$Nv^S$ of the present invention are:

a) constructing a natural, synthetic or semi-synthetic DNA encoding said PBP protein;

b) integrating said DNA into an expression vector in a manner suitable for expressing said PBP protein, as the natural protein product or as a fusion protein;

c) transforming or otherwise introducing said vector into an appropriate eucaryotic or prokaryotic host cell forming a recombinant host cell, d) culturing said recombinant host cell in a manner enabling expression of said protein; and e) recovering and substantially purifying said protein by any suitable means, well known to those skilled in the art.

Expressing Recombinant PBP Proteins in Procaryotic and Eucaryotic Host Cells

In general, procaryotes are used for cloning DNA sequences and for constructing the vectors of the present invention. Procaryotes may also be employed in the production of a novel PBP protein of the present invention. For example, the *Escherichia coli* K12 strain 294 (ATCC No. 31446) is particularly useful for the prokaryotic expression of foreign proteins. Other strains of *E. coli*, bacilli such as *Bacillus subtilis*, enterobacteriaceae such as *Salmonella typhimurium* or *Serratia marcescans*, various Pseudomonas species and other bacteria, such as Streptomyces, may also be employed as host cells in the cloning and expression of the recombinant proteins of this invention.

Promoter sequences suitable for driving the expression of genes in procaryotes include β-lactamase [e.g. vector pGX2907, ATCC 39344, contains a replicon and β-lactamase gene], lactose systems [Chang et al., Nature-(London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other promoters, such as that from bacteriophage T7, whose nucleotide sequences are generally known, enable one of skill in the art to ligate such promoter sequences to DNA encoding the proteins of the instant invention using linkers or adapters to supply any required restriction sites. Still other promoters are useful for gene expression in *S. pneumoniae*, for example the ami promoter (J. P. Claverys et al."Construction and evaluation of new drug-resistance cassettes for gene disruption mutagenesis in *Streptococcus pneumoniae* , using an ami test platform." Gene (1995) 123–128) Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) that cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to procaryotes, a variety of eucaryotic microorganisms such as yeast are suitable host cells. The yeast Saccharomyces cerevisiae is the most commonly used eucaryotic microorganism. A number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced PBP-Nv and PBP-$Nv^S$

An expression vector carrying cloned pbp-nv or pbp-$nv^S$ of *Streptococcus pneumoniae* is transformed or transfected into a suitable host cell using standard methods. Cells that contain the vector are propagated under conditions suitable for expression of the encoded PBP. If the gene is under the control of an inducible promoter, suitable growth conditions would incorporate an appropriate inducer. Recombinantly-produced PBP-$Nv^S$ or PBP-Nv protein may be purified from cellular extracts of transformed cells by any suitable means. Recombinantly-produced PBP-Nv is expected to be partially localized in the host cell membrane. As such, PBP-Nv is recoverable from cell extracts and cell membranes by any suitable means, well known to those skilled in the art.

In a preferred process for protein purification the gene encoding the PBP of the present invention is modified at the 5' end to incorporate several histidine residues at the amino terminal end of the encoded protein product. The "histidine tag" enables a simplified protein purification method referred to as "immobilized metal ion affinity chromatography" (IMAC), essentially as described in U.S. Pat. No. 4,569,794, which hereby is incorporated by reference. The IMAC method enables rapid isolation of substantially pure protein starting from a crude cellular extract.

Other embodiments of the present invention comprise isolated nucleic acid sequences. As skilled artisans will recognize, owing to the degeneracy of the genetic code the amino acid compounds of the invention can be encoded by a multitude of different nucleic acid sequences. Because these alternative nucleic acid sequences would encode the same amino acid sequences, the present invention further comprises these alternate nucleic acid sequences.

The nucleic acid sequences encoding SEQ ID NO:2, and disclosed subregions therein may be produced using synthetic methodology. The synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the pbp-nv or related gene sequence pbp-$nv^S$ could be generated using a conventional DNA synthesizing apparatus, such as the Applied Biosystems Model 380A or 380B DNA synthesizers (Applied Biosystems, Inc., 850 Lincoln Center Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach*, (1984).]

In an alternative and preferred methodology, namely PCR, the DNA sequence comprising a portion or all of SEQ ID NO:1 can be generated from *Streptococcus pneumoniae* genomic DNA using suitable oligonucleotide primers complementary to SEQ ID NO:1 or region therein, as described in U.S. Pat. No. 4,889,818, which hereby is incorporated by reference. Suitable protocols for performing the PCR are widely known and are disclosed in, for example, *PCR Protocols: A Guide to Method and Applications*, Ed. Michael A. Innis et al., Academic Press, Inc. (1990).

The ribonucleic acids of the present invention may be prepared using the polynucleotide synthetic methods discussed supra, or they may be prepared enzymatically using RNA polymerase to transcribe a suitable DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of the template to be transcribed. See, J. Sambrook, et al., supra, at 18.82–18.84.

This invention also provides nucleic acids, RNA or DNA, that are complementary to SEQ ID NO:1 or SEQ ID NO:3.

The present invention also provides probes and primers useful for a variety of molecular biology techniques including, for example, hybridization screens of genomic or subgenomic libraries. A nucleic acid compound comprising SEQ ID NO:1, SEQ ID NO:3 or a complementary sequence thereof, or a fragment thereof, and which is at least 18 base pairs in length, and which will selectively hybridize to *Streptococcus pneumoniae* DNA or mRNA encoding the PBP of the present invention, is provided. Preferably, the 18 or more nucleotide bases are DNA. These probes and primers can be prepared by enzymatic methods well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those that comprise DNA. The most preferred recombinant DNA vectors comprise the isolated DNA sequence, SEQ ID NO:1. Plasmid JAH142 is an especially preferred DNA vector for expressing the soluble form of the PBP of this invention in *E. coli*.

The skilled artisan understands that choosing the most appropriate cloning vector or expression vector depends upon a number of factors including the availability of restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance and metabolic markers of one type and another), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. The skilled artisan will recognize a number of inducible promoters that respond to a variety of inducers, for example, carbon source, metal ions, heat, and others. The practitioner also understands that the amount of nucleic acid or protein to be produced dictates, in part, the selection of the expression system. The addition of certain nucleotide sequences is useful for directing the localization of a recombinant protein. For example, a sequence encoding a signal peptide preceding the coding region of a gene, is useful for directing the extra-cellular export of a resulting polypeptide.

Host cells harboring the nucleic acids disclosed herein are also provided by the present invention. A preferred host is *E. coli* that has been transfected or transformed with a vector that comprises a nucleic acid of the present invention.

The present invention also provides a method for constructing a recombinant host cell capable of expressing SEQ ID NO:2, or the soluble form thereof, said method comprising transforming or otherwise introducing into a host cell a recombinant DNA vector that comprises an isolated DNA sequence which encodes SEQ ID NO:2 or fragment thereof. The preferred host cell is any strain of *E. coli* that can accomodate high level expression of an exogenously introduced gene. Preferred vectors for expression are those which comprise SEQ ID NO:1. An especially preferred expression vector for use in *E. coli* is pJAH142, which comprises nucleotide residues 232 through 2193 of SEQ ID NO:1. (See FIGURE). Transformed host cells may be cultured under conditions well known to skilled artisans such that a recombinant protein is expressed, thereby producing in the recombinant host cell the PBP of the instant invention.

For the purpose of identifying or developing new antibiotic compounds it is useful to determine compounds that bind to PBPs and/or inhibit the transpeptidase or transglycosylase activity. The instant invention provides a screen for identifying compounds that bind PBP-Nv and/or PBP-$Nv^S$ or fragment thereof, said screen comprising the steps of:

a) preparing and substantially purifying a recombinant PBP of the invention;

b) exposing said PBP to a test compound; and c) monitoring, by any suitable means, the binding by said compound to said PBP, or inhibition of enzymatic activity of said PBP by said compound.

The substrate for a transglycosylase assay can be made according to art-recognized methods (See e.g. DiBerardino et al. FEBS Letters, 392, 184–88 (1996). For example, the lipid precursor substrate can be prepared from *Streptococcus pneumoniae* membranes, or from the membranes of any other suitable bacteria, UDP-Mur-Nac-pentapeptide, and UDP-N-acetyl[$^{14}$C]glucosamine (Amersham, Buckinghamshire, UK). Transglycosylase activity is measured by the production of the peptidoglycan polymerization product essentially by mixing the substrate with a source of PBP and monitoring the amount of [$^{14}$C]-label in the peptidoglycan.

The above-disclosed screening system could also be used to identify compounds that inhibit the transpeptidase activity of PBP-NV or PBP-$Nv^S$. In a preferred embodiment of this aspect of the invention compounds are tested for their ability to competitively inhibit the binding of labeled penicillin to PBP-Nv or PBP-$Nv^S$.

The screening system described above provides a means to determine compounds that interact with the PBPs of the present invention and which may interfere with peptidoglycan biosynthesis. This screening method may be adapted to automated procedures such as a PANDEX® (Baxter-Dade Diagnostics) system, allowing for efficient high-volume screening for potential inhibitory agents.

The following examples more fully describe the present invention. Those skilled in the art will recognize that the particular reagents, equipment, and procedures described below are merely illustrative and are not intended to limit the present invention in any manner.

EXAMPLE 1

Construction of a DNA Vector for Expressing *Streptococcus pnuemoniae* pbp-$nv^S$ Gene in a Heterologous Host Plasmid JAH142 (See FIGURE) is an approximately 7300 base pair expression vector suitable for expressing a modified pbp-$nv^S$ in procaryotic host *E. coli*. This plasmid contains an origin of replication (Ori), an ampicillin resistance gene (Amp), useful for selecting cells that have incorporated the vector following a tranformation procedure, and further comprises the T7 promoter in operable linkage to the coding region of said PBP gene. Parent plasmid pET11 A (obtained from Novogen, Madison, Wis.) was linearized by digestion with endonucleases NdeI and HindIII. Linearized pET11A was ligated to a DNA fragment bearing NdeI and HindIII sticky ends, comprising a modified pbp-$nv^S$ gene. The pbp-$nv^S$ gene ligated into pJAH142 was modified at the 5' end in order to simplify purification of the encoded protein product. For this purpose, an oligonucleotide encoding 8 histidine residues and a factor Xa cleavage site, Ile-Glu-Gly-Arg, was inserted at the 3' end of an ATG start codon and at the 5' end of residue 232 of SEQ ID NO: 1. Placement of the histidine residues at the amino terminus of the encoded protein enables the IMAC protein purification procedure (See Example 4). An additional modification of the pbp-$nv^S$ gene ligated into pJAH142 comprises two silent base pair substitutions, one at nucleotide residue 270 of SEQ ID NO.1, at which a "G" replaces an "A", and the other at nucleotide residue 777 of SEQ ID NO.1, at which a "C" replaces a "T." These substitutions do not alter the encoded amino acid sequence.

EXAMPLE 2

Construction of a DNA Vector for Expression of pbp-nv in a heterologous host The plasmid construction method outlined in Example 1 is followed to construct a vector for expressing PBP-Nv in a heterologous host such as *E. coli*. A "his-tag" oligonucleotide comprising the same structure and sequence disclosed in Example 1 is inserted at the 3' end of the ATG initiation codon at nucleotide position 3 of SEQ ID NO.1.

EXAMPLE 3

Expression of Streptococcus pneumoniae pbp-nvSGene in *Echerichia coli*

Expression plasmid JAH142 was transformed into *E. coli* BL21 (DE3) ($F^-ompT[lon]hsdS\ r_B^-m_B^-$) using standard methods (See e.g. Sambrook et al. Supra). Transformants, chosen at random were tested for the presence of pJAH142 by agarose gel electrophoresis using quick plasmid preparations. Id. Transformants were grown overnight at 37° C. in LB medium supplemented with 100 μg/ml ampicillin. The overnight culture was diluted into fresh LB medium and allowed to grow to an $O.D._{600}$ of 0.4 to 0.6. At that point, expression of the vector-bound pbp-nvS gene was induced by adding 0.4 mM IPTG for a period of 3 hours. The induced-culture was then pelleted by centrifugation in preparation for protein purification (See Example 4).

EXAMPLE 4

Purification of PBP-$Nv^S$

The recombinant cell pellet, isolated as described in the last step of Example 3, was resuspended in 60 ml of 20 mM potassium phosphate, pH 7.5. The cells were disrupted by passage through a French press, producing a cell extract that was centrifuged at 150,000×g for 1 hour. The supernatant was loaded onto a 200 ml bed-volume XK50 source-Q column (Pharmacia) equilibrated in 20 nM potassium phosphate, pH 7.5 (buffer A). The column was washed with 500 ml buffer A and eluted with a linear gradient of 0 to 1M KCl in buffer A. Fractions were pooled, tested for penicillin binding activity, and the fractions showing binding activity were dialyzed overnight at 4° C. against 20 mM potassium phosphate, pH 7 (buffer B). The dialyzed protein sample was applied to a XK26 hydroxyapatite column (60 ml bed volume) equilibrated in buffer B. After washing the column with buffer B, samples were eluted with a linear gradient of 20 mM to 700 mM potassium phosphate, pH 7. Fractions exhibiting penicillin binding activity were pooled and dialzyed against 20 mM Tris, pH 8.

The PBP-Nv$^S$ protein contained in the pooled fractions was purified further by immobilized metal ion affinity chromatography (IMAC), essentially as described in U.S. Pat. No. 4,569,794, the entire contents of which is hereby incorporated by reference. Briefly, the IMAC procedure involved adding to the protein sample the following components at the indicated final concentrations: 0.5M NaCl, 5 mM imidazole. The sample was loaded onto a Chelating Sepharose Fast Flow column (Pharmacia, 10 ml bed volume) and the column washed twice with 35 ml each of 20 mM Tris, pH 8, 0.5 M NaCl and 5 mM imidazole; 20 mM Tris, pH 8, 0.5 M NaCl and 60 mM imidazole. The bound protein was eluted from the column with 20 mM Tris, pH 8, 0.5 M NaCl, 1 M imidazole. Six fractions of 3 ml each were collected and tested for penicillin binding activity (See Example 5).

EXAMPLE 5

Penicillin binds*Streptococcus pneumoniae* PBP-Nv

Protein fractions isolated from the IMAC column, as in Example 4, are tested for penicillin binding as follows. About 10 ul of the protein sample eluted from the column is mixed with $^{125}$I-labeled penicillin V at a final concentration of 48 ug/ml. Labeled penicillin is prepared as described in Blasczak et al. "Radioiododestannylation. Convenient synthesis of a stable penicillin derivative for rapid penicillin binding protein assay," J. Labelled Compd. Radiopharm. 27, 401–06 (1989). About 3 ul of a 1 ug/ul solution of sodium clavulanate is added to prevent degradation of the labeling reagent. The mixture is incubated at 35° C. for 15 minutes. Reactions are terminated by the addition of one-half volume SDS with boiling for 2 minutes. Aliquots of each mixture are fractionated by polyacrylamide gel electrophoresis, and radiolabeled bands are detected by exposure to X-ray film.

This method demonstrates a major labeled band at about 72 kilodalton (the predicted size based on amino acid sequence disclosed in SEQ ID NO2 ).

EXAMPLE 6

Determination of PBP-Nv Transglycosylase activity

Radiolabelled lipid precursor for use as substrate is prepared as described in H. Hara and H. Suzuki FEBS Lett. 168, 155–60 (1984). Peptidoglycan synthesis activities are determined in 50 μl reactions containing 50 mM PIPES, pH 6.1, 10 mM $MgCl_2$, 0.2 mM DTT, 1 mM ATP, 26% DMSO, PBP-Nv or PBP-Nv$^S$ sample and $^{14}$C-labelled lipid precursor. The reaction is incubated for 30 minutes at room temperature and filtered through hydrophilic Durapore PVDF membranes (0.65 μm; Millipore, Bedford, MA). Under these conditions the synthesized peptidoglycan is retained while the unincorporated labeled substrate is washed through using 0.4 M ammonium acetate in methanol. The filter bound radioactivity is determined by scintillation counting.

We claim:

1. An isolated nucleic acid compound encoding a protein having the amino acid sequence which is SEQ ID NO 2.

2. An isolated nucleic acid compound encoding a substantially sure Penicillin Binding Protein Nv soluble (PBP-$Nv^s$) having the amino acid sequence that is defined by residues 78 through 731 of SEQ ID NO 2.

3. An isolated nucleic acid compound comprising a sequence encoding a protein having the amino acid sequence which is SEQ ID NO.2 wherein said compound has a sequence selected from the group consisting of:

(a)

| | | | | | | |
|---|---|---|---|---|---|---|
| ATGAAATTAG | ATAAATTATT | TGAGAAATTT | CTTTCTCTTT | TTAAAAAAGA | AACAAGTGAA | 60 |
| CTAGAGGACT | CTGATTCTAC | TATCTTACGT | CGCTCTCGTA | GTGATCGAAA | AAAATTAGCC | 120 |
| CAAGTAGGTC | CGATTCGAAA | ATTCTGGCGT | CGTTATCATC | TAACAAAGAT | TATCCTTATA | 180 |
| CTAGGTTTGA | GTGCAGGCTT | GCTAGTTGGA | ATCTATTTGT | TTGCTGTAGC | CAAGTCGACC | 240 |
| AATGTCAATG | ATTTGCAAAA | TGCCTTGAAA | ACTCGGACTC | TTATTTTTGA | CCGTGAAGAA | 300 |
| AAAGAGGCTG | GTGCCTTGTC | TGGTCAAAAG | GGAACCTATG | TTGAGCTGAC | TGACATCAGT | 360 |
| AAAAACTTGC | AGAATGCTGT | TATTGCGACA | GAAGACCGTT | CTTTCTATAA | AAATGACGGG | 420 |
| ATTAACTATG | GCCGTTTCTT | CTTGGCTATT | GTCACTGCTG | GACGTTCAGG | TGGTGGCTCT | 480 |
| ACCATTACCC | AACAGCTGGC | TAAAAACGCC | TATTTATCGC | AGGATCAAAC | TGTTGAGAGA | 540 |
| AAAGCGAAAG | AATTTTTCCT | TGCCTTAGAA | TTAAGCAAAA | AATATAGTAA | GGAGCAAATT | 600 |
| CTAACCATGT | ACCTTAACAA | CGCTTATTTT | GGAAATGGTG | TGTGGGGTGT | AGAAGATGCG | 660 |
| AGTAAGAAAT | ACTTTGGAGT | TTCTGCATCA | GAAGTGAGTC | TGGATCAAGC | TGCGACTCTG | 720 |
| GCAGGGATGC | TCAAGGGGCC | GGAACTGTAT | AATCCCTTGA | ATTCCGTAGA | AGATTCTACT | 780 |
| AATCGGCGCG | ATACTGTCTT | GCAGAATATG | GTTGCAGCAG | GATATATTGA | TAAAAACCAA | 840 |
| GAAACCGAAG | CTGCTGAAGT | TGATATGACT | TCGCAATTGC | ACGATAAGTA | TGAAGGAAAA | 900 |
| ATCTCAGATT | ACCGTTACCC | CTCTTATTTT | GATGCGGTGG | TTAATGAAGC | TGTTTCCAAG | 960 |
| TATAATCTAA | CAGAGGAAGA | GATTGTCAAT | AATGGCTACC | GCATTTACAC | AGAGCTGGAC | 1020 |
| CAAAACTACC | AAGCAAATAT | GCAGATTGTT | TATGAAAACA | CATCGCTATT | TCCGAGGGCA | 1080 |
| GAGGATGGAA | CGTTTGCTCA | ATCAGGAAGT | GTAGCTCTCG | AACCGAAAAC | AGGGGGAGTT | 1140 |
| CGTGGAGTTG | TCGGTCAAGT | TGCTGACAAT | GATAAAACTG | GATTCCGGAA | TTTCAACTAT | 1200 |
| GCAACCCAAT | CAAAGCGTAG | TCCTGGTTCT | ACAATTAAGC | CTTTAGTTGT | TTATACACCA | 1260 |
| GCAGTTGAAG | CAGGCTGGGC | TTTGAATAAG | CAGTTGGATA | ACCATACCAT | GCAGTATGAT | 1320 |
| AGCTATAAGG | TTGATAACTA | TGCAGGGATC | AAAACAAGTC | GAGAAGTTCC | TATGTATCAA | 1380 |
| TCCTTGGCAG | AATCGCTTAA | TCTACCTGCT | GTTGCCACTG | TTAATGATTT | GGGTGTTGAC | 1440 |
| AAGGCTTTTG | AGGCAGGCGA | AAAATTCGGA | CTCAACATGG | AAAAGGTCGA | CCGTGTTCTT | 1500 |
| GGTGTCGCCT | TGGGAAGCGG | TGTTGAAACC | AACCCTCTTC | AAATGGCTCA | AGCATACGCT | 1560 |
| GCCTTTGCAA | ATGAAGGTTT | AATGCCTGAA | GCTCATTTTA | TTAGTAGAAT | TGAAAATGCT | 1620 |
| AGTGGACAAG | TTATTGCGAG | TCATAAAAAT | TCACAAAAAC | GGGTGATTGA | TAAGTCTGTA | 1680 |
| GCTGACAAGA | TGACCAGTAT | GATGTTGGGG | ACTTTCACCA | ACGGTACCGG | TATTAGTTCA | 1740 |
| TCGCCTGCAG | ACTATGTCAT | GGCAGGGAAA | ACTGGAACAA | CTGAAGCAGT | TTTCAATCCG | 1800 |
| GAGTACACAA | GTGACCAGTG | GGTAATTGGT | TATACTCCGG | ATGTAGTGAT | TAGCCACTGG | 1860 |
| CTTGGCTTTC | CGACCACTGA | TGAAAATCAC | TATCTAGCTG | GCTCTACTTC | AAACGGTGCA | 1920 |
| GCTCATGTCT | TTAGAAACAT | TGCCAATACT | ATTTTACCTT | ATACGCCAGG | AAGTACCTTT | 1980 |
| ACGGTTGAAA | ATGCTTATAA | GCAAAATGGA | ATTGCACCAG | CCAATACAAA | AAGACAAGTA | 2040 |
| CAAACCAATG | ATAATAGCCA | GACAGATGAT | AATTTGTCTG | ATATTCGAGG | GCGTGCGCAA | 2100 |
| AGTCTAGTAG | ATGAGGCTAG | CCGGGCTATC | TCAGATGCGA | AGATTAAGGA | AAAGGCTCAA | 2160 |
| ACAATATGGG | ATTCGATAGT | CAATCTATTT | CGC | | | 2193 |

which is SEQ ID NO:1;

(b)

```
AUGAAAUUAG AUAAAUUAUU UGAGAAAUUU CUUUCUCUUU UUAAAAAAGA AACAAGUGAA   60
CUAGAGGACU CUGAUUCUAC UAUCUUACGU CGCUCUCGUA GUGAUCGAAA AAAAUUAGCC  120
CAAGUAGGUC CGAUUCGAAA AUUCUGGCGU CGUUAUCAUC UAACAAAGAU UAUCCUUAUA  180
CUAGGUUUGA GUGCAGGCUU GCUAGUUGGA AUCUAUUUGU UUGCUGUAGC CAAGUCGACC  240
AAUGUCAAUG AUUUGCAAAA UGCCUUGAAA ACUCGGACUC UUAUUUUUGA CCGUGAAGAA  300
AAAGAGGCUG GUGCCUUGUC UGGUCAAAAG GGAACCUAUG UUGAGCUGAC UGACAUCAGU  360
AAAAACUUGC AGAAUGCUGU UAUUGCGACA GAAGACCGUU CUUUCUAUAA AAAUGACGGG  420
AUUAACUAUG GCCGUUUCUU CUUGGCUAUU GUCACUGCUG GACGUUCAGG UGGUGGCUCU  480
ACCAUUACCC AACAGCUGGC UAAAAACGCC UAUUUAUCGC AGGAUCAAAC UGUUGAGAGA  540
AAAGCGAAAG AAUUUUUCCU UGCCUUAGAA UUAAGCAAAA AAUAUAGUAA GGAGCAAAUU  600
CUAACCAUGU ACCUUAACAA CGCUUAUUUU GGAAAUGGUG UGUGGGGUGU AGAAGAUGCG  660
AGUAAGAAAU ACUUUGGAGU UUCUGCAUCA GAAGUGAGUC UGGAUCAAGC UGCGACUCUG  720
GCAGGGAUGC UCAAGGGGCC GGAACUGUAU AAUCCCUUGA AUUCCGUAGA AGAUUCUACU  780
AAUCGGCGCG AUACUGUCUU GCAGAAUAUG GUUGCAGCAG GAUAUAUUGA UAAAAACCAA  840
GAAACCGAAG CUGCUGAAGU UGAUAUGACU UCGCAAUUGC ACGAUAAGUA UGAAGGAAAA  900
AUCUCAGAUU ACCGUUACCC CUCUUAUUUU GAUGCGGUGG UUAAUGAAGC UGUUUCCAAG  960
UAUAAUCUAA CAGAGGAAGA GAUUGUCAAU AAUGGCUACC GCAUUUACAC AGAGCUGGAC 1020
CAAAACUACC AAGCAAAUAU GCAGAUUGUU UAUGAAAACA CAUCGCUAUU UCCGAGGGCA 1080
GAGGAUGGAA CGUUUGCUCA AUCAGGAAGU GUAGCUCUCG AACCGAAAAC AGGGGGAGUU 1140
CGUGGAGUUG UCGGUCAAGU UGCUGACAAU GAUAAAACUG GAUUCCGGAA UUUCAACUAU 1200
GCAACCCAAU CAAAGCGUAG UCCUGGUUCU ACAAUUAAGC CUUUAGUUGU UUAUACACCA 1260
GCAGUUGAAG CAGGCUGGGC UUUGAAUAAG CAGUUGGAUA ACCAUACCAU GCAGUAUGAU 1320
AGCUAUAAGG UUGAUAACUA UGCAGGGAUC AAAACAAGUC GAGAAGUUCC UAUGUAUCAA 1380
UCCUUGGCAG AAUCGCUUAA UCUACCUGCU GUUGCCACUG UUAAUGAUUU GGGUGUUGAC 1440
AAGGCUUUUG AGGCAGGCGA AAAAUUCGGA CUCAACAUGG AAAAGGUCGA CCGUGUUCUU 1500
GGUGUCGCCU UGGGAAGCGG UGUUGAAACC AACCCUCUUC AAAUGGCUCA AGCAUACGCU 1560
GCCUUUGCAA AUGAAGGUUU AAUGCCUGAA GCUCAUUUUA UUAGUAGAAU UGAAAAUGCU 1620
AGUGGACAAG UUAUUGCGAG UCAUAAAAAU UCACAAAAAC GGGUGAUUGA UAAGUCUGUA 1680
GCUGACAAGA UGACCAGUAU GAUGUUGGGG ACUUUCACCA ACGGUACCGG UAUUAGUUCA 1740
UCGCCUGCAG ACUAUGUCAU GGCAGGGAAA ACUGGAACAA CUGAAGCAGU UUUCAAUCCG 1800
GAGUACACAA GUGACCAGUG GGUAAUUGGU UAUACUCCGG AUGUAGUGAU UAGCCACUGG 1860
CUUGGCUUUC CGACCACUGA UGAAAAUCAC UAUCUAGCUG GCUCUACUUC AAACGGUGCA 1920
GCUCAUGUCU UUAGAAACAU UGCCAAUACU AUUUUACCUU AUACGCCAGG AAGUACCUUU 1980
ACGGUUGAAA AUGCUUAUAA GCAAAAUGGA AUUGCACCAG CCAAUACAAA AAGACAAGUA 2040
CAAACCAAUG AUAAUAGCCA GACAGAUGAU AAUUUGUCUG AUAUUCGAGG GCGUGCGCAA 2100
AGUCUAGUAG AUGAGGCUAG CCGGGCUAUC UCAGAUGCGA AGAUUAAGGA AAAGGCUCAA 2160
ACAAUAUGGG AUUCGAUAGU CAAUCUAUUU CGC                              2193
```

which is SEQ ID NO:3 and;

(c) a nucleic acid compound fully complementary to (a) or (b).

4. An isolated nucleic acid compound comprising a sequence encoding a protein having the amino acid sequence which is defined by residues 78 through 731 of SEQ ID NO.2 wherein said compound has a sequence selected from the group consisting of:

(a) residues 232 through 2193 of SEQ ID NO.1;

(b) residues 232 through 2193 of SEQ ID NO.3 and;

(c) a nucleic acid compound fully complementary to (a) or (b).

5. An isolated nucleic acid compound of claim 3 wherein the sequence of said compound is SEQ ID NO:1 or a sequence fully complementary to SEQ ID NO:1.

6. An isolated nucleic acid compound of claim 3 wherein the sequence of said compound is SEQ ID NO:3 or a sequence fully complementary to SEQ ID NO:3.

7. A vector comprising an isolated nucleic acid compound of claim 3.

8. A vector comprising an isolated nucleic acid compound of claim 4.

9. A vector, as in claim 7, wherein said isolated nucleic acid compound is SEQ ID NO 1 operably linked to a promoter sequence.

10. A vector, as in claim 8, wherein said isolated nucleic acid compound comprises residues 232 through 2193 of SEQ ID NO. 1 operably linked to a promoter sequence.

11. A host cell containing a vector of claim 7.

12. A host cell containing a vector of claim 9.

13. A host cell containing a vector of claim 10.

14. A method for constructing a recombinant host cell having the potential to express PBP-$Nv^S$ having the amino acid sequence which is SEQ ID NO:2, said method comprising introducing into a host cell by any suitable means a vector of claim 7.

15. A method for expressing PBP-$Nv^S$ the amino acid sequence which is SEQ ID NO:2 in the recombinant host cell of claim 14, said method comprising culturing said recombinant host cell under conditions suitable for gene expression.

16. A method for constructing a recombinant host cell having the potential to express PBP-$Nv^S$ having the amino acid sequence which is SEQ ID NO:2, said method comprising introducing into a host cell by any suitable means a vector of claim 10.

17. An isolated nucleic acid compound, useful as a probe, said compound comprising at least 18 nucleotide bases, and consisting of a sequence that is contiguous fragment of SEQ ID NO.1 or SEQ ID NO.3.

* * * * *